United States Patent
Mattiuz et al.

(10) Patent No.: US 7,384,983 B2
(45) Date of Patent: Jun. 10, 2008

(54) INHIBITOR OF MONOAMINE UPTAKE

(75) Inventors: Edward Louis Mattiuz, Fishers, IN (US); John-Michael Sauer, Indianapolis, IN (US); William Joe Wheeler, Indianapolis, IN (US); David Taiwai Wong, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 269 days.

(21) Appl. No.: 11/125,348

(22) Filed: May 9, 2005

(65) Prior Publication Data

US 2005/0209341 A1 Sep. 22, 2005

Related U.S. Application Data

(63) Continuation of application No. 10/468,553, filed as application No. PCT/US02/03385 on Feb. 20, 2002, now abandoned.

(60) Provisional application No. 60/273,730, filed on Mar. 6, 2001.

(51) Int. Cl.
*A61K 31/135* (2006.01)
*C07C 213/00* (2006.01)
(52) U.S. Cl. ............... 514/646; 514/649; 514/651; 564/280

(58) Field of Classification Search ............... 514/651
See application file for complete search history.

(56) References Cited

U.S. PATENT DOCUMENTS

| | | | |
|---|---|---|---|
| 4,314,081 A | | 2/1982 | Molloy et al. |
| 2004/0082666 A1* | | 4/2004 | Mattiuz et al. ......... 514/651 |

FOREIGN PATENT DOCUMENTS

| | | | |
|---|---|---|---|
| EP | 0303961 A | | 2/1989 |
| WO | WO02070457 | * | 9/2002 |

OTHER PUBLICATIONS

Ring et al, Identification of the Human Cytochromes P450 Responsible for Atomoxetine Metabolism, Drug Metabolism and Disposition, 2001, vol. 30 No. 3, 319-23.*
Farid, et al. (1985) "Single-Dose and Steady-State Pharmacokinetics of Tomoxetine in Normal Subjects" *J Clin Pharmacol*; 25: 296-301.
Ring, et al. (2001) "Identification of the Human Cytochromes P450 Responsible for Atomoxetine Metabolism" *Drug Metabolism and Disposition*; vol. 30, No. 3: 319-323.

* cited by examiner

*Primary Examiner*—Alton Pryor
(74) *Attorney, Agent, or Firm*—Charles E. Cohen; David M. Stemerick

(57) ABSTRACT

The present invention provides compounds and methods for the inhibition of monoamine uptake in mammals.

6 Claims, No Drawings

INHIBITOR OF MONOAMINE UPTAKE

This application is a CON of 10/468,553 filed on 08/21/2003, now abndoned, which is the U.S. National stage entry of PCT1U501103385, filed on 02/20/2002, under 35 USC 371 which claims the benefit of U.S. Provisional Application number 60/273,730 filed 3/6/01 .

The relationship between monoamine uptake and a number of neurological disorders in mammals has been established, and the 3-aryloxy-3-substituted-1-aminopropanes have demonstrated remarkable diversity in their ability to inhibit the uptake of monoamines. Certain members of the 3-aryloxy-3-substituted-1-aminopropane class have found utility in the treatment of neurological disorders. Fluoxetine, N-methyl 3-((4-trifluoromethylphenyl)oxy)-3-phenyl-1-aminopropane hydrochloride, for example, is a selective serotonin uptake inhibitor that has found great market acceptance in the treatment of depression and has been approved for the treatment of a number of other disorders. Atomoxetine, (−)-N-methyl 3-((2-methylphenyl)oxy)-3-phenyl-1-aminopropane hydrochloride, is a selective norepinephrine uptake inhibitor that is being investigated clinically for the treatment of attention deficit/hyper-activity disorder. Duloxetine, (+)-N-methyl 3-(1-naphthalenyloxy)-3-(2-thienyl)-1-aminopropane hydrochloride, inhibits the uptake of both norepinephrine and serotonin and is presently in clinical evaluation for the treatment of depression. These compounds are among many 3-aryloxy-3-substituted-1-aminopropanes taught in U.S. Pat. Nos. 4,018,895, 4,194,009, 4,314,081, 4,956,388, and 5,023,269. The utility of a hydroxylated 3-phenoxy-3-phenyl-1-aminopropane, however, has heretofore not been appreciated.

The present invention provides a compound of Formula I:

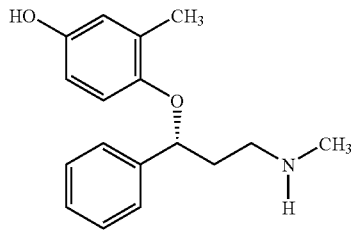

I or a pharmaceutically acceptable salt thereof.

This invention also provides a pharmaceutical formulation that comprises, in association with a pharmaceutically acceptable carrier, diluent or excipient, a compound of Formula I.

The present invention provides a method for inhibiting the uptake of norepinephrine and serotonin in mammals comprising administering to a mammal in need of such inhibition a pharmaceutically effective amount of a compound of Formula I.

A further embodiment of this invention is a method for inhibiting the uptake of norepinephrine and serotonin in mammals for treating a variety of disorders that have been linked to decreased neurotransmission of serotonin and/or norepinephrine in mammals. These disorders include: depression, migraine pain, bulimia, premenstrual syndrome or late luteal phase syndrome, alcoholism, tobacco abuse, panic disorder, anxiety, general pain, post-traumatic syndrome, memory loss, dementia of aging, social phobia, attention deficit/hyperactivity disorder, psoriasis, oppositional defiant disorder, conduct disorder, borderline personality disorder, obsessive compulsive disorder, chronic fatigue syndrome, premature ejaculation, erectile difficulty, anorexia nervosa, disorders of sleep, autism, mutism, allergic rhinitis, cold symptoms, narcolepsy, incontinence, trichotillomania, trigeminal neuralgia, dental pain or temperomandibular joint dysfunction pain. Any of these methods employ a compound of Formula I.

This invention also provides the use of a compound of Formula I for the manufacture of a medicament for the inhibition of norepinephrine and serotonin uptake. Additionally, this invention provides a pharmaceutical formulation adapted for the inhibition of norepinephrine and serotonin uptake containing a compound of Formula I or a metabolic precursor thereof.

The present invention further provides a method for the preparation of a compound of Formula I comprising the steps of:

a) coupling a compound of formula (i)

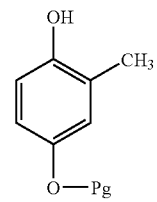

(i)

where "Pg" is an oxygen protecting group, with 1-chloro-3-phenyl-3-hydroxypropane to provide a compound of formula (ii):

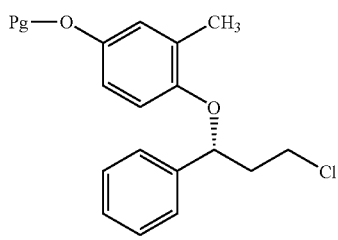

(ii)

where "Pg" is an oxygen protecting group;

b) reacting a compound of formula (ii) with a source of iodide ion to provide a compound of formula (iii):

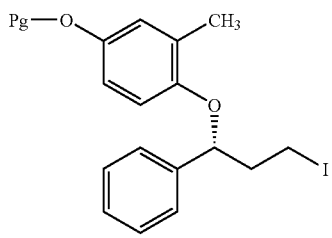

where "Pg" is an oxygen protecting group;
c) reacting a compound of formula (iii) with methylamine to provide R-(−)-N-methyl 3-((2-methyl-4-hydroxyphenyl)oxy)-3-phenyl-1-aminopropane; and
d) optionally treating R-(−)-N-methyl 3-((2-methyl-4-hydroxyphenyl)oxy)-3-phenyl-1-aminopropane with a pharmaceutically acceptable acid.

The present invention also provides a process for the preparation of a compound of Formula I comprising the steps of:
a) coupling a compound of formula (i)

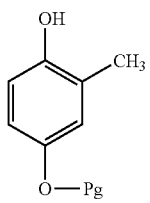

where "Pg" is an oxygen protecting group, with (S)-1-phenyl-3-methylaminopropan-1-ol to provide a compound of formula (iv):

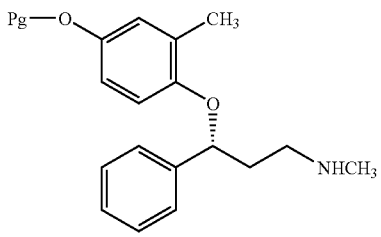

where "Pg" is an oxygen protecting group;
b) reacting a compound of formula (iv) with a deprotecting agent to provide R-(−)-N-methyl 3-((2-methyl-4-hydroxyphenyl)oxy)-3-phenyl-1-aminopropane; and
c) optionally treating R-(−)-N-methyl 3-((2-methyl-4-hydroxyphenyl)oxy)-3-phenyl-1-aminopropane with a pharmaceutically acceptable acid.

Compounds of formula (ii), (iii), and (iv) are useful intermediates for the preparation of compounds of Formula I, and represent further embodiments of the present invention.

The compound of Formula I is generally referred to as R-(−)-N-methyl 3-((2-methyl4-hydroxyphenyl)oxy)-3-phenyl-1-aminopropane. Because this compound is an amine, it is basic in nature and accordingly reacts with any of a number of inorganic and organic acids to form pharmaceutically acceptable acid addition salts. It is preferable to convert the free amine to a pharmaceutically acceptable acid addition salt for ease of handling and administration. Acids commonly employed to form salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid and oxalic acid.

The compound of Formula I is chiral, and may be prepared by chiral chromatography of the racemic or enantiomerically enriched forms of a compound of Formula I, or fractional crystallization of salts prepared from racemic or enantiomerically enriched free amine and a chiral acid. Alternatively, the free amine may be reacted with a chiral auxiliary and the enantiomers separated by chromatography followed by removal of the chiral auxiliary to regenerate the free amine. Furthermore, separation of enantiomers may be performed at any convenient point in the synthesis of the compounds of the invention. Preferably, the compounds of the invention are prepared beginning with chiral starting material.

The present invention provides a method for the inhibition of serotonin and norepinephrine uptake. These mechanisms are operable in mammals, and the preferred mammal is human.

The 3-aryloxy-3-substituted-1-aminopropane structural class of compounds has historically been an attractive target for synthesis, and a number of useful syntheses have been described in the literature. The syntheses of atomoxetine (R-(−)-N-methyl 3-((2-methylphenyl)oxy)-3-phenyl-1-aminopropane, formerly known as tomoxetine) and fluoxetine, for example, are described in *Tetrahedron Letters*, 30(39), 5207 (1989); *Tetrahedron Letters*, 35(9), 1339 (1994); *Tetrahedron*, 53(20), 6739 (1997); WO 99/18947; WO 00/58262; and WO 00/61540. R-(−)-N-methyl 3-((2-methyl-4-hydroxyphenyl)oxy)-3-phenyl-1-aminopropane may be conveniently prepared as illustrated in the following scheme where "Pg" is an oxygen protecting group and "X" is either chloro or NHMe.

Scheme I

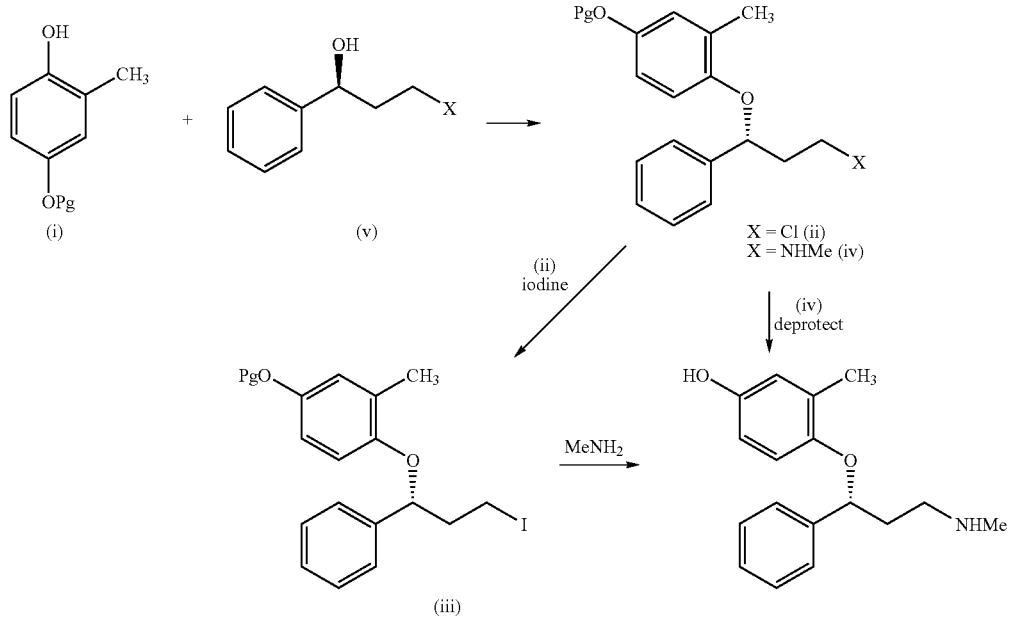

The requisite phenols of formula (i) may be prepared from commercially available methylhydroquinone by introducing an appropriate oxygen-protecting group by standard synthetic methods. Suitable oxygen protecting groups for phenols are well known to the skilled artisan and are described in Greene and Wuts (*Protective Groups in Organic Synthesis*, Third Edition, John Wiley and Sons, New York (1999)). Preferred protecting groups for the process of the present invention are alkanoyl esters and silyl ethers. Particularly preferred oxygen protecting groups are acetyl, tert-butoxycarbonyl, and tert-butyldimethylsilyl. The use of tert-butoxycarbonyl is especially preferred.

The compounds of formula (v) are well known in the art and may be prepared by standard synthetic methods. Syntheses of 1-phenyl-1-hydroxy-3-chloropropane (v, X=Cl) have been reported by Corey and Reichard (*Tetrahedron Letters*, 30(39), 5207-5210 (1989)); Srebnik, et al (*Journal of Organic Chemistry*, 53, 2916-2020 (1988)); and Schneider and Goergens (*Tetrahedron Asymmetry*, 3(4), 525-528 (1992)). Syntheses of 1-phenyl-1-hydroxy-3-(methylamino)propane (v, X=NHMe) have been reported by Koenig and Mitchell (*Tetrahedron Letters*, 35(9), 1339-1342 (1994)); Gao and Sharpless (*Journal of Organic Chemistry*, 53, 4081-4084 (1988)); and in EP 0 909 754 A1.

An appropriate phenol (i) is coupled with either 1-phenyl-1-hydroxy-3-chloropropane (v, X=Cl) or with 1-phenyl-1-hydroxy-3-(methylamino)propane (v, X=NHMe) in the presence, of a dialkyl azodicarboxylate and triphenylphosphine under standard Mitsunobu coupling conditions to provide the aryl ether (ii) or the aryl ether (iv), respectively. Typically a solution of an equivalent of phenol (i) and an equivalent of alcohol (v) are combined in a suitable solvent with from about 1.0 to about 1.1 equivalents of triphenylphosphine. Suitable solvents include any solvent that dissolves a sufficient amount of the reactants to allow the reaction to occur without significantly interfering with the desired reaction. Suitable solvents include dioxane, diethyl ether, and tetrahydrofuran. A preferred solvent is tetrahydrofuran. This solution is cooled to from about −5° C. to about 5° C., preferably from about 0C to about 5° C. The reaction mixture is. maintained under an inert atmosphere of either nitrogen or argon. About 1.0 to about 1.5 equivalents, preferably about 1.1 equivalents, of a dialkyl azodicarboxylate, preferably diisopropyl azodicarboxylate, are added to the reaction mixture. The resulting mixture is then stirred for from about 1 hour to about 24 hours and then the desired aryl ether is isolated and purified by standard techniques.

A solution of aryl ether (ii) in a suitable solvent, preferably acetone, is treated with from about one molar equivalent to a large excess of a source of iodide ion. Any source of iodide ion that is compatible with the chosen solvent and aryl ether (ii) is acceptable. Preferred sources of iodide ion include sodium and potassium iodide. Sodium iodide is a preferred source of iodide ion. The resulting aryl ether (iii) is isolated and purified by standard techniques.

A solution of aryl ether (iii) in a suitable solvent, typically tetrahydrofuran, is reacted with from about an equivalent to a large excess of methylamine. Methylamine may be added as a gas, condensed into the reaction mixture as a liquid, or added as an aqueous solution to the reaction mixture. Once the addition is complete, the reactants are stirred together for from about one hour to about 24 hours. The desired amine is then isolated and purified by standard techniques. The skilled artisan will appreciate that, depending on the nature of the particular oxygen protecting group (Pg) employed, either a compound of formula (iv) or R-(−)-N-methyl 3-((2-methyl-4-hydroxyphenyl)oxy)-3-phenyl-1-aminopropane will be recovered by this step. For example, when Pg is acetyl, the protecting group is removed during the amination step.

When the particular protecting group (Pg) of a compound of formula (iv) must be removed in a separate step, the skilled artisan will appreciate that the specific conditions for regenerating the phenol moiety depend on the nature of the protecting group. Standard methods for the removal of oxygen-protecting groups are described in Greene and Wuts, supra. When Pg is tert-butyldimethylsilyl, for example, the protecting group is conveniently removed by treating the starting silyl ether (iv) with a source of fluoride ion in a suitable solvent. Alternatively, where Pg is tert-butoxycarbonyl, the protecting group is conveniently removed by treatment with acid, typically hydrochloric acid. The resulting R-(−)-N-methyl 3-((2-methyl-4-hydroxyphenyl)oxy)-3-phenyl-1-aminopropane may then be isolated and purified by standard techniques.

The following preparations and examples more specifically illustrate embodiments of the present invention and the preparation of R-(−)-N-methyl 3-((2-methyl-4-hydroxyphenyl)oxy)-3-phenyl-1-aminopropane.

Preparation I 4-acetoxy-2-methylphenol

Acetic anhydride (4.73 gm, 4.37 mL, 46.3 mMol) was added dropwise to a mixture of 4-hydroxy-2-methylphenol (5 gm, 46.3 mMol) and cesium carbonate (15.1 gm, 46.3 mMol) in acetonitrile (50 mL). After stirring overnight, the mixture was filtered and the filtrate was concentrated under reduced pressure. The residue was subjected to silica gel chromatography, eluting with 5:1 pentane:ethyl acetate. Fractions containing product were combined and concentrated under reduced pressure to provide 0.24 gm (3%) of the desired compound.

$^1$H-NMR(CDCl$_3$) δ 1.54 (1H, bs), 2.18 (3H, s), 2.22 (3H, s), 6.59 (1H, m), 6.65 (1H, m), 6.82 (1H, m).

Preparation II (S)-3-chloro-1-phenyl-1-propanol

To a solution of (S)-1-phenyl-1,3-propanediol (125 g, 0.822 mole) in methyl tert-butyl ether (500 mL) was added triethylamine (135 mL). The reaction mixture was cooled to 0° C. and a solution of 4-bromobenzenesulfonyl chloride (230 g, 0.92 mole) in methyl tert-butyl ether (300 mL) and tetrahydrofuran (300 mL) was added dropwise over 3 hour. After the addition, the reaction mixture was stirred at 0° C. for three hours and was then warmed to ambient temperature. After stirring at ambient temperature for 18 hours, benzyltriethylammonium chloride (210 g, 0.92 mole) was added and the resulting mixture was heated at 55° C. for three hours. The reaction mixture was cooled to ambient temperature and then diluted with water. After separation of the organic phase, the aqueous phase was extracted two times with diethyl ether. The combined organic extracts were washed with 1.0 N hydrochloric acid, saturated aqueous sodium bicarbonate, water, saturated aqueous sodium chloride, dried over magnesium sulfate, and concentrated under reduced pressure to provide an off-white solid (160 g). This solid was subjected to silica gel chromatography, eluting with ethyl acetate/hexane (1:9) to provide 110 grams (80%) of the title compound.

$^1$H-NMR (CDCl$_3$) (400 MHz) δ: 2.20 (m, 1H), 2.45 (m, 1H), 3.60 (m, 1H), 3.75 (m, 1H), 4.95 (m, 1H), 7.45 (m, 5H).

MS(FAB): m/z=172.0 (10%), 170 (23%), 154 (10%), 132 (25%), 117 (5%), 107 (100%), 79 (54%), 77 (45%), 51 (19%).

Preparation III 4-((tert-butoxycarbonyl)oxy)-2-methylphenol

Di-tert-butoxycarbonate (52.4 g, 0:24 mol) in tetrahydrofuran (100 ml) was added dropwise to a solution of methylhydroquinone (99.2 g, 0.80 mol) and dimethylaminopyridine (4.8 g, 4.0 mmol) in diethyl ether (1.1 L) at ambient temperature. After stirring for 40 minutes, the reaction mixture was quenched with 1 N hydrochloric acid (200 ml). The organic layer was separated, washed with saturated aqueous sodium chloride (200 ml), dried over sodium sulfate and concentrated to a crude oil that solidified on standing. Purification of the crude solid by Biotage Flash 75 chromatography eluting with 94/6 hexane/ethyl acetate (94/6) yielded an off-white solid which was recrystallized from dichloromethane/hexane (15/85) to provide 28.5 (53%) of the title compound.

$^1$H-NMR (CDCl$_3$) δ: (300 MHz) 1.55 (s, 9H), 2.22 (s, 3H), 4.76 (s, 1H), 6.68 (d, J=8.78 Hz, 1H), 6.85 (dd, J=8.78 Hz and 2.92 Hz, 1H), 6.92 (d, J=2.92 Hz, 1H).

MS(FAB): m/z=225.3, 211.3, 169.3, 155.2, 124.2.

EXAMPLE 1

R-(−)-N-methyl 3-((2-methyl-4-hydroxyphenyl) oxy)-3-phenyl-1-aminopropane oxalate (R)-3-chloro-1-phenyl-1-(2-methyl-4-acetoxyphenoxy)propane A solution of (S)-(−)-3-chloro-1-phenyl-1-propanol (0.204 gm, 1.20 mMol), 4-acetoxy-2-methylphenol (0.200 gm, 1.20 mMol) and triphenylphosphine (0.346 g, 1.32 mMol) in 10 mL tetrahydrofuran was cooled to 0-5° C. under argon. This mixture was treated dropwise with di-isopropylazodicar-boxylate (0.26 mL, 1.32 mMol) in tetrahydrofuran (2 mL). The resulting mixture was stirred for 1 hour at 0-5° C. and was then allowed to warm to room temperature. After stirring at room temperature over night the reaction mixture was concentrated under reduced pressure and the residue triturated with 10% ethyl acetate in pentane and stirred until the suspended solid was crystalline. The suspension was filtered and the recovered crystalline solid washed with 10% ethyl acetate in pentane. The combined filtrates were concentrated under reduced pressure and the residue subjected to silica gel chromatography eluting with toluene. Fractions containing product were combined and concentrated under reduced pressure to provide 0.205 gm (54%) of the desired compound as a pale yellow oil.

MS(FD): m/e=318 (M$^+$)

(R)-3-iodo-1-phenyl-1-(2-methyl-4-acetoxyphenoxy) propane

A mixture of (R)-3-chloro-1-phenyl-1-(2-methyl-4-acetoxyphenoxy)propane (0.200 gm, 0.63 mMol) and 15 mL acetone saturated with potassium iodide was stirred at reflux under argon overnight. The reaction mixture was poured into 50 mL diethyl ether and the resulting suspension was filtered. The filtrated was washed with saturated aqueous sodium hydrogen sulfite followed by water. The remaining organic phase was dried over magnesium sulfate and concentrated under reduced pressure to provide 0.18 gm (70%) of the desired compound as a colorless oil.

MS(FD): m/e=410 (M$^+$)

Amination

A mixture of (R)-3-iodo-1-phenyl-1-(2-methyl-4-acetoxyphenoxy)propane (0.180 gm, 0.44 mMol) and 40% aqueous methylamine (5 mL, 71 mMol) in 15 mL tetrahydrofuran was stirred at room temperature overnight. The reaction mixture was concentrated under reduced pressure and the residue partitioned between water and ethyl acetate. The ethyl acetate phase was washed with water, dried over magnesium sulfate, and concentrated under reduced pressure. The residue was dissolved in ethyl acetate and treated with oxalic acid (0.04 gm, 0.44 mMol). The resulting white solid was recovered by filtration, washed with ethyl acetate and dried under reduced pressure to provide 0.107 gm (67%) of the title compound.

MS(FD): m/e=271 (M$^+$)

EA: Calculated for $C_{19}H_{23}NO_6$: Theory: C, 63.15; H, 6.41; N, 3.88. Found: C, 63.32;

H, 6.59; N, 3.99.

EXAMPLE 2

R-(−)-N-methyl 3-((2-methyl-4-hydroxyphenyl)oxy)-3-phenyl-1-aminopropane hydrochloride (R)-3-chloro-1-phenyl-1-(2-methyl-4-O-tert-butoxycarboxy-phenoxy)propane An oven dried, three-necked, 2-L, round-bottomed flask was charged with (S)-3-chloro-1-phenyl-propanol (52 g, 304 mmol), 4-((tert-butoxycarbonyl)oxy)-2-methylphenol (73.86 g, 329 mmol), triphenylphosphine (87.36 g, 333 mmol) and anhydrous tetrahydrofuran (600 ml). The reaction mixture was cooled at 0° C., and a solution of diisopropylazadicarbox-ylate (76 ml, 365 mmol,) in dry tetrahydrofuran (100 mL) was added over 6 hours. The reaction mixture was stirred for an additional two hours at 0° C. and was then allowed to warm gradually to room temperature. The reaction mixture was further stirred at room temperature for 24 hours and the reaction mixture was concentrated under reduced pressure. The residue was treated with 2 L of 9:1 pentane:ethyl acetate. The resulting suspension was stored at −20° C. for 24 hours and the insoluble materials were removed by filtration. The precipitate was washed with 9:1 pentane:ethyl acetate (200 mL). The combined filtrates were concentrated under reduced pressure. The crude residue (150 grams) was purified by 150 flash Biotage prepacked column eluting with 3% ethyl acetate in hexane to provide (R)-3-chloro-1-phenyl-1-(2-methyl-4-((tert-butoxycarbonyl)oxy)-phenoxy)propane (100 g) in 85% yield.

$^1$H-NMR (CDCl$_3$) δ: (400 MHz) 1.50 (s, 9H), 2.20 (m, 1H), 2.27 (s, 3H), 2.46 (m, 1H), 3.60 (m, 1H), 3.76 (m, 1H), 5.31 (m, 1H), 6.56 (d, J=8.8 Hz, 1H), 6.72 (m, 1H), 7.24 (m, 1H), 7.32 (s, 4H).

$^3$C-NMR (CDCl$_3$) δ: (75 MHz) 15.27, 16.59, 27.69, 41.25, 41.48, 83.20, 113.15, 113.71, 118.42, 118.84, 122.21, 123.42, 125.39, 125.81, 127.93, 128.17, 128.80, 140.77, 144.29, 152.46, 153.44.

MS(FAB): m/z=376.145.

EA: Calculated for $C_{21}H_{25}ClO_4$: C, 66.93; H, 6.69; Cl, 9.41. Found: C, 66.94; H, 6.74; Cl, 9.67.

(R)-3-iodo-1-phenyl-1-(2-methyl-4-((tert-butoxycarbonyl)-oxy)phenoxy)propane

A dry 1-L R.B. flask was charged (R)-3-chloro-1-phenyl-1-(2-methyl-4-((tert-butoxycarbonyl)oxy)phenoxy)propane (18.00 g, 47.80 mmol), sodium iodide (90.0 g, 600 mmol) and 2-butanone (550 mL). The reaction flask was protected from light. The reaction mixture was stirred at reflux temperature under nitrogen for 16 hours. The mixture was cooled to room temperature and poured into ether (1 L). The insoluble inorganic salts (white precipitate) were removed by filtration. The filtrate was concentrated under reduced pressure and the crude residue was dissolved in diethyl ether (1 L). The ethereal layer was washed with cold saturated sodium bisulfite solution (2×200 mL), water and saturated aqueous sodium chloride. The organic layer was dried over anhydrous magnesium sulfate and concentrated under reduced pressure. The residue was subjected to flash chromatography, eluting with 20% ethyl acetate in hexane to provide 20.5 grams (91%) of the desired compound.

$^1$H-NMR (CDCl$_3$ 400 MHz) δ 1.56 (s, 9H),.2.30 (s, 3H), 2.40 (1H, m), 2.50 (1H, m), 3.25 (m, 1H), 3.35 (m, 1H), 5.21 (m, 1H), 6.55 (d, J=8.8, 1H), 6.75 (m, 1H), 6.95 (d, J=2.4 Hz, 1H), 7.25 (m, 1H), 7.37 (m, 4H).

MS(FAB): m/z=468.0 (100%), 342 (10%).

EA: Calcd for $C_{21}H_{25}IO_4$: C, 53.86, H, 5.38. Found: C, 53.36, H, 4.79.

Amination/Deprotection/Salt Formation (R)-3-iodo-1-phenyl-1-(2-methyl-4-((tert-butoxy-carbonyl)oxy)phenoxy)propane (20.0 g, 42.66 mmol) was dissolved in anhydrous tetrahydrofuran (100 mL). The solution was treated with methylamine (300 mL, 2M solution in tetrahydrofuran) under nitrogen atmosphere and the reaction stirred at ambient temperature for 15 hours at which time the reaction mixture was concentrated to dryness. The residue was treated with ethyl acetate and cold water. The two layers were separated. The aqueous layer was extracted with ethyl acetate. The combined organic layers were washed thoroughly with a cold saturated sodium bisulfite solution, cold water, dried over magnesium sulfate, and concentrated under reduced pressure. The residue was dissolved in ethyl acetate. The solution was extracted with ice-cold 0.1 N hydrochloric acid. Lyophilization of the aqueous solution yielded a yellow solid which was dissolved in methanol, and passed through a short column of activated carbon, Norit, 100 mesh powder (2% charcoal). The solvent was removed and resulting hydrochloride salt precipitated upon trituration with a minimal amount of water. The hydrochloride salt was recrystallized from water to provide the desired product (7.22 g, 55%).

$^1$H-NMR (DMSO 300 MHz) δ 2.12 (m, 1H), 2.15 (s, 3H), 2.20 (m, 1H), 2.49 (s, 3H), 2.99 (m, 2H), 5.31 (m, 1H), 6.33 (dd, J=8.7 Hz and 2.56 Hz, 1H), 6.51 (m, 1H), 7.29 (m, 1H), 7.34 (m, 5H), 8.77 (s, 1H), 8.85 (br s, 1H).

MS(FAB): m/z=272.4.

EA: Calcd for $C_{17}H_{21}NO_2$—HCl: C, 66.33, H, 7.20. N, 4.55, Cl, 11.52. Found: C, 66.23, H, 7.22, N, 5.37, Cl, 11.23.

All of the compounds concerned are orally available and are normally administered orally, and so oral administration is preferred. However, oral administration is not the only route or even the only preferred route. For example, transdermal administration may be very desirable for patients who are forgetful or petulant about taking oral medicine. Compounds of Formula I may also be administered by the percutaneous, intravenous, intramuscular, intranasal or intrarectal route, in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

A formulation useful for the administration of R-(−)-N-methyl 3-((2-methylphenyl)oxy)-3-phenyl-1-aminopropane hydrochloride (atomoxetine), a metabolic precursor of R-(−)-N-methyl 3-((2-methyl-4-hydroxyphenyl)oxy)-3-phenyl-1-aminopropane, comprises a dry mixture of R-(−)-N-methyl 3-((2-methylphenyl)oxy)-3-phenyl-1-aminopropane hydrochloride with a diluent and lubricant. A starch, such as pregelatinized corn starch, is a suitable diluent and a silicone oil, such as dimethicone, a suitable lubricant for use in hard gelatin capsules. Suitable formulations are prepared containing about 0.4 to 26% R-(−)-N-methyl 3-((2-methylphenyl)oxy)-3-phenyl-1-aminopropane hydrochloride, about 73 to 99% starch, and about 0.2 to 1.0% silicone oil. The following tables illustrate particularly preferred formulations:

|  | 2.5 mg | 5 mg | 10 mg | 18 mg | 20 mg | 25 mg | 40 mg | 60 mg |
| --- | --- | --- | --- | --- | --- | --- | --- | --- |
| Ingredient (%) |  |  |  |  |  |  |  |  |
| R-(—)-N-methyl 3-((2-methylphenyl)oxy)-3-phenyl-1-aminopropane hydrochloride | 1.24 | 2.48 | 4.97 | 8.94 | 9.93 | 12.42 | 19.87 | 22.12 |
| Dimethicone | 0.5 | 0.5 | 0.5 | 0.5 | 0.5 | 0.5 | 0.5 | 0.5 |
| Pregelatinized Starch | 98.26 | 97.02 | 94.53 | 90.56 | 89.57 | 87.08 | 79.63 | 77.38 |
| Ingredient (mg/capsule) |  |  |  |  |  |  |  |  |
| R-(—)-N-methyl 3-((2-methylphenyl)oxy)-3-phenyl-1-aminopropane hydrochloride | 2.86 | 5.71 | 11.43 | 20.57 | 22.85 | 28.57 | 45.71 | 68.56 |
| Dimethicone | 1.15 | 1.15 | 1.15 | 1.15 | 1.15 | 1.15 | 1.15 | 1.55 |
| Pregelatinized Starch | 225.99 | 223.14 | 217.42 | 208.28 | 206.00 | 200.28 | 183.14 | 239.89 |
| Capsule Fill Weight (mg) | 230 | 230 | 230 | 230 | 230 | 230 | 230 | 310 |
| Capsule Size | 3 | 3 | 3 | 3 | 3 | 3 | 3 | 2 |

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the formula I, or its pharmaceutical salt, from about 0.1 to about 10% w/v (weight per unit volume).

The skilled artisan will appreciate that R-(−)-N-methyl 3-((2-methyl-4-hydroxyphenyl)oxy)-3-phenyl-1-aminopropane may be obtained by the conversion, for example by enzymatic or acid catalysis, of metabolic precursors of R-(−)-N-methyl 3-((2-methyl-4-hydroxyphenyl)oxy)-3-phenyl-1-aminopropane. A metabolic precursor of R-(−)-N-methyl 3-((2-methyl-4-hydroxyphenyl)oxy)-3-phenyl-1-aminopropane is a compound that is converted to R-(−)-N-methyl 3-((2-methyl-4-hydroxyphenyl)oxy)-3-phenyl-1-aminopropane in vivo after administration of the metabolic precursor to a mammal. Therefore, in addition to the methods described in the preceding paragraphs, administration of R-(−)-N-methyl 3-((2-methyl-4-hydroxyphenyl)oxy)-3-phenyl-1-aminopropane may also be accomplished by administering a metabolic precursor of R-(−)-N-methyl 3-((2-methyl-,4-hydroxyphenyl)oxy)-3-phenyl-1-aminopropane. Such metabolic precursor would be administered in dosage amounts that would produce effective inhibition of serotonin and norepinephrine uptake without causing harmful or untoward side effects.

Metabolic precursors of R-(−)-N-methyl 3-((2-methyl-4-hydroxyphenyl)oxy)-3-phenyl-1-aminopropane include carboxylic acid esters, sulfonate esters, amino acid esters, and ethers of the hydroxy moiety of Formula I. Furthermore, it has been discovered that R-(−)-N-methyl 3-((2-methyl-4-hydroxyphenyl)oxy)-3-phenyl-1-aminopropane can be obtained by the enzymatic conversion of R-(−)-N-methyl 3-((2-methyl-phenyl)oxy)-3-phenyl-1-aminopropane, atomoxetine, in vivo. Therefore, a preferred method of systemic administration of R-(−)-N-methyl 3-((2-methyl-4-hydroxyphenyl-yl)oxy)-3-phenyl-1-aminopropane is the oral administration to mammals of R-(−)-N-methyl 3-((2-methyl-phenyl)oxy)-3-phenyl-1-aminopropane hydrochloride, atomoxetine. That is, systemic administration of R-(−)-N-methyl 3-((2-methyl-4-hydroxyphenyl)oxy)-3-phenyl-1-aminopropane may be preferably accomplished by oral administration to mammals of R-(−)-N-methyl 3-((2-methylphenyl)oxy)-3-phenyl-1-aminopropane hydrochloride, atomoxetine, as a metabolic precursor of R-(−)-N-methyl 3-((2-methyl-4-hydroxyphenyl)-oxy)-3-phenyl-1-aminopropane.

Microdialysis Assays of Monoamines

Sprague-Dawley rats (Harlan or Charles River) weighing 270-300 grams are surgically implanted with microdialysis probes under chloral hydrate/pentobarbital anesthesia (170 and 36 mg/kg i.p. in 30% propylene glycol, 14% ethanol) as described by Perry and Fuller. (Perry and Fuller, Effect of fluoxetine on serotonin and dopamine concentration in rat hypothalamus after administration of fluoxetine plus L-5-hydroxytryptophan, *Life Sci.*, 50, 1683-90 (1992)). A David Kopf stereotaxic instrument is used to implant the probe unilaterally in the hypothalamus at coordinates rostral −1.5 mm, lateral −1.3 mm, and ventral −9.0 mm (Paxinos and Watson, 1986). After a 48-hour recovery period, rats are placed in a large plastic bowl with a mounted liquid swivel system (CMA/120 system for freely moving animals, Bioanalytical Systems, West Lafayette, Ind.). Filtered artificial cerebrospinal fluid (CSF) (150 mM NaCl, 3.0 MM KCl, 1.7 mM CaCl2, and 0.9 mM MgCl2) is perfused through the probe at a rate of 1.0 ml/min. The output dialysate line is fitted to a tenport HPLC valve with a 20 µl loop. At the end of each 30 minute sampling period, dialysate collected in the loop is injected on an analytical column (Spherisorb 3 µ ODS2, 2×150 mm, Keystone Scientific).

The method used to measure monoamines is as described by Perry and Fuller (1992). Briefly, dialysate collected in the 20 µl loop is assayed for 5-HT and NE. The 20 µl injection goes onto the column with a mobile phase which resolves NE and 5-HT: 75 mM potassium acetate, 0.5 mM ethylenediaminetetraacetic acid, 1.4 mM sodium octanesulfonic acid and 8% methanol, pH 4.9. The mobile phase for the amine column is delivered with a flow programmable pump at an initial flow rate of 0.2 ml/min increasing to 0.3 ml/min at 5 min then decreasing back to 0.2 ml/min at 26 min with a total run time of 30 min. Flow programming is used to elute the 5-HT within a 25 min time period. The electrochemical detector (EG&G, Model 400) for the amine column is set at a potential of 400 mV and a sensitivity of 0.2 nA/V. Basal levels are measured for at least 90 minutes prior to drug administration. The drugs are prepared in filtered deionized water (volume 0.25-0.3 ml) for administration at the desired doses.

R-(−)-N-methyl 3-((2-methyl-4-hydroxyphenyl)oxy)-3-phenyl-1-aminopropane was tested essentially as described above and was found to inhibit the uptake of both serotonin ($K_i$=43 nM) and norepinephrine ($K_i$=3.0 nM).

Metabolism of R-(−)-N-methyl 3-((2-methyl-4-phenyl)oxy)-3-phenyl-1-aminopropane to R-(−)-N-methyl 3-((2-methyl-4-hydroxyphenyl)oxy)-3-phenyl-1-aminopropane in humans An open-label study was performed in seven healthy men CYP2D6 genotype was identified as EM (extensive metabolizer) or PM (poor metabolizer) prior to study start. CYP2D6 is an enzyme with genetic polymorphism resulting in at least 2 populations of individuals with either active or poor metabolic capabilities. The majority of people are designated "extensive metabolizers" (EM) and possess "normal" CYP2D6 activity. Mutations or deletion of the CYP2D6 gene results in a minority of people (5% to 10% of Caucasians; 1% of Asians) who are known as "poor metabolizers" (PM) of CYP2D6 substrates.

Multiple 20-mg doses of R-(−)-N-methyl 3-((2-methylphenyl)oxy)-3-phenyl-1-aminopropane were administered twice daily over 5 days followed by a single radiolabeled tomoxetine 20-mg dose (actual dose 19.66 mg) on the morning of the $6^{th}$ day. Radiolabeled [3-$^{14}$C]—R-(−)-N-methyl 3-((2-methylphenyl)oxy)-3-phenyl-1-aminopropane was supplied as 20-mg capsules of R-(−)-N-methyl 3-((2-methylphenyl)oxy)-3-phenyl-1-aminopropane hydrochloride containing a sufficient quantity of [3-$^{14}$C]—R-(−)-N-methyl 3-((2-methylphenyl)oxy)-3-phenyl-1-aminopropane hydrochloride to provide a dose of approximately 3.7 Mbq (100 µCi).

Approximately 12 hours after the morning dose on Days 1 through 5, a second 20-mg capsule was administered with 240 mL of water. This evening dose was administered at least 30 minutes after a low residue evening meal. On the morning of Day 6, a capsule of 20-mg R-(−)-N-methyl 3-((2-methylphenyl)oxy)-3-phenyl-1-aminopropane hydrochloride containing 100 µCi [3-$^{14}$C]—R-(−)-N-methyl 3-((2-methylphenyl)oxy)-3-phenyl-1-aminopropane hydrochloride was given orally with 240 mL of water 30 minutes after completion of a standardized breakfast.

Whole blood samples were collected from EM subjects 12 hours prior to and immediately before administration of [3-$^{14}$C]—R-(−)-N-methyl 3-((2-methylphenyl)oxy)-3-phenyl-1-aminopropane hydrochloride (predose control sample), and at approximately 1, 2, 3, 4, 6, 8, 12, 18, 24, 36, 48, and 72 hours after dosing. Whole blood samples were collected from PM subjects 12 hours prior to and immediately before administration of [3-$^{14}$C]—R-(−)-N-methyl 3-((2-methylphen-yl)oxy)-3-phenyl-1-aminopropane hydrochloride (predose control sample), and at approximately 1, 2, 3, 4, 6, 8, 12, 18, 24, 48, 72, 96, 120, 144, 168, 192, and 216 hours after dosing. Whole blood samples (approximately 12 mL) were collected at each timepoint into glass tubes containing heparin as an anticoagulant. Whole blood samples were stored on ice-until centrifuged. For preparing plasma, the blood was centrifuged at approximately 3000 rpm for approximately 15 minutes at approximately 4° C. within 1 hour of collection. Aliquots of plasma were removed for determination of radioequivalent concentrations. Remaining plasma was stored at approximately −70° C. prior to assay for conjugated and unconjugated N-methyl 3-((2-methylphen-yl)oxy)-3-phenyl-1-aminopropane, R-(−)-N-methyl 3-((2-methyl-4-hydroxyphenyl)oxy)-3-phenyl-1-aminopropane, 3-((2-methylphenyl)oxy)-3-phenyl-1-aminopropane concentrations or metabolite profiling.

Heparinized human plasma samples were analyzed for N-methyl 3-((2-methylphenyl)oxy)-3-phenyl-1-aminopropane, R-(−)-N-methyl 3-((2-methyl-4-hydroxy-phenyl)oxy)-3-phenyl-1-aminopropane, and using a validated APCI LC/MS/MS (atmospheric pressure chemical ionization liquid chromatography/mass spectrometry/mass spectrometry) method over the concentration ranges 1.00 to 800.00 ng/mL for N-methyl 3-((2-methylphenyl)oxy)-3-phenyl-1-aminopropane and R-(−)-N-methyl 3-((2-methyl-4-hydroxyphenyl)oxy)-3-phenyl-1-aminopropane, and 2.50 to 2000.00 ng/mL for 3-((2-methylphenyl)oxy)-3-phenyl-1-aminopropane. Further analysis was conducted using a lower range validated APCI LC/MS/MS method over the concentration ranges 1.00 to 100.00 ng/mL for R-(−)-N-methyl 3-((2-methylphenyl)oxy)-3-phenyl-1-aminopropane and R-(−)-N-methyl 3-((2-methyl-4-hydroxyphenyl)oxy)-3-phenyl-1-aminopropane and 0.25 to 25.00 ng/mL for R-(−)-3-((2-methylphenyl)oxy)-3-phenyl-1-aminopropane.

The primary metabolite of R-(−)-N-methyl 3-((2-methylphenyl)oxy)-3-phenyl-1-aminopropane hydrochloride produced by both CYP2D6 EM and PM subjects is R-(−)-N-methyl 3-((2-methyl-4-hydroxyphenyl)oxy)-3-phenyl-1-aminopropane. The EM subjects metabolized 86.5% of R-(−)-N-methyl 3-((2-methylphenyl)oxy)-3-phenyl-1-aminopropane hydrochloride to R-(−)-N-methyl 3-((2-methyl-4-hydroxyphenyl)oxy)-3-phenyl-1-aminopropane. The PM subjects metabolized 40% of R-(−)-N-methyl 3-((2-methylphenyl)oxy)-3-phenyl-1-aminopropane hydrochloride to R-(−)-N-methyl 3-((2-methyl4-hydroxyphenyl-yl)oxy)-3-phenyl-1-aminopropane.

We claim:

1. An isolated, purified compound of Formula I:

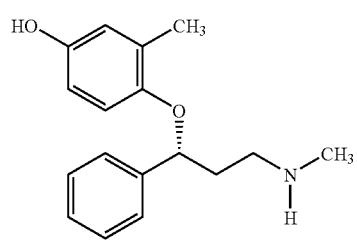

I or a pharmaceutically acceptable salt thereof.

2. The compound R-(−)-N-methyl 3-((2-methyl-4-hydroxyphenyl)oxy)-3-phenyl-1-aminopropane hydrochloride.

3. A pharmaceutical formulation, comprising a compound of Formula I:

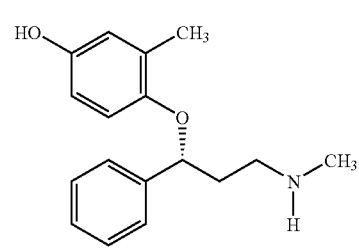

I or a pharmaceucically acceptable salt thereof, in association with a pharmaceutically acceptable carrer, diluent, or excipient.

4. A pharmaceutical formulation of claim 3, where the compound of Formula I is R-(−)-N-methyl 3-((2methyl-4-hydroxyphenyl)oxy)-3-phenyl-1-aminopropane hydrochloride.

5. A method for inhibiting the uptake of norepinephrine and serotonin in mammals, comprising administering to a mammal in need of such inhibition a pharmaceutically effective amount of a compound of Formula I:

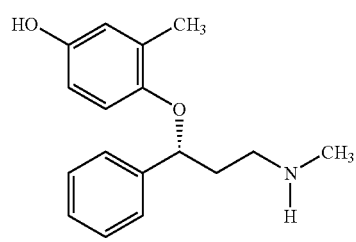

I or a pharmaceutically acceptable salt thereof.

6. The method of claim 5, wherein said compound of Formula I is R-(−)-N-methyl 3-((2-methyl-4-hydroxyphenyl)oxy)-3-phenyl-1-aminopropane hydrochloride.

* * * * *

UNITED STATES PATENT AND TRADEMARK OFFICE
CERTIFICATE OF CORRECTION

| | | |
|---|---|---|
| PATENT NO. | : 7,384,983 B2 | Page 1 of 1 |
| APPLICATION NO. | : 11/125348 | |
| DATED | : June 10, 2008 | |
| INVENTOR(S) | : Edward Louis Mattiuz | |

It is certified that error appears in the above-identified patent and that said Letters Patent is hereby corrected as shown below:

Column 16:
In Claim 3, line 25, below the drawing, a roman number I should be centered below the drawing. This roman numeral was left out.

Column 16:
In Claim 3, line 28, carrer should be spelled carrier

Column 16:
In Claim 4, line 33, it should read compound of Formula I is R-(-)-N-methyl 3-((2-methyl-4- instead of R-(-)-N-methyl 3-((2methyl-4-

Column 16:
In Claim 6, line 65 it should read nyl)oxy)-3-phenyl-1-aminopropane hydrochloride, instead of nyl)oxy)-3-phenyl-l-aminopropane hydrochloride Signed and Sealed this Ninth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,384,983 B2 Page 1 of 1
APPLICATION NO. : 11/125348
DATED : June 10, 2008
INVENTOR(S) : Edward Louis Mattiuz et al.

It is certified that error appears in the above-identified patent and that said Letters Patent is hereby corrected as shown below:

Col. 15, Claim 1, line 56, the Figure identifier is misplaced to the right of the column. The Roman numeral "I" should be moved from the right of the column to be centered below the drawing at line 65.

Col. 16, Claim 3, line 13, the Figure identifier is misplaced to the right of the column. The Roman numeral "I" should be moved from the right of the column to be centered below the drawing at line 23.

Col. 16, Claim 5, line 47, the Figure identifier is misplaced to the right of the column. The Roman numeral "I" should be moved from the right of the column to be centered below the drawing at line 56.

Signed and Sealed this

Ninth Day of June, 2009

JOHN DOLL
*Acting Director of the United States Patent and Trademark Office*